United States Patent [19]

Stahly

[11] Patent Number: 4,538,006

[45] Date of Patent: Aug. 27, 1985

[54] AROMATIC COUPLING PROCESS

[75] Inventor: G. Patrick Stahly, Baton Rouge, La.

[73] Assignee: Ethyl Corporation, Richmond, Va.

[21] Appl. No.: 606,952

[22] Filed: May 4, 1984

[51] Int. Cl.$^3$ .............................................. C07C 79/24
[52] U.S. Cl. ................................... 568/707; 568/710; 568/711
[58] Field of Search ............... 568/704, 706, 707, 744, 568/711, 710

[56] References Cited

U.S. PATENT DOCUMENTS

| 2,712,151 | 10/1955 | Kehe | 568/744 |
| 2,716,667 | 8/1955 | Hodge | 568/707 |
| 3,015,676 | 1/1962 | Johnson | 568/744 |
| 4,105,699 | 8/1978 | Stark | 568/744 |
| 4,172,151 | 10/1979 | Moore | 424/330 |

FOREIGN PATENT DOCUMENTS 2336551 12/1979 Fed. Rep. of Germany ...... 568/710

OTHER PUBLICATIONS

Wright et al., "J. Organic Chem.", vol. 33(3), 1245–1246, (1968).
Kornblum et al., "J. Organic Chem", vol. 41(9), pp. 1560–1564, (1976).
Caronna et al., "Tetrahedron Letters", No. 7, pp. 657–660, (1979), Pergamon Press Ltd., Great Britain.

*Primary Examiner*—Werren B. Lone
*Attorney, Agent, or Firm*—Donald J. Johnson; John F. Sieberth; Patricia J. Hogan

[57] ABSTRACT 4-(2,4-Dinitrophenyl)phenols are prepared by reacting a 1,3-dinitrobenzene having a replaceable hydrogen in the 4-position with a phenol having a replaceable hydrogen in the 4-position in an inert solvent and in the presence of a strong base. The 1,3-dinitrobenzene and phenol may be substituted or unsubstituted, and preferred phenols include phenol and 2,6-dialkylphenols.

9 Claims, No Drawings

AROMATIC COUPLING PROCESS

FIELD OF INVENTION

This invention relates to 4-(2,4-dinitrophenyl)phenols and more particularly to a process for preparing them.

BACKGROUND

As indicated in Caronna et al., *Tetrahedron Letters*, No. 7, pp. 657–660 (1979), U.S. Pat. No. 4,172,151 (Moore), and German Offenlegungsschrift No. 2,336,551 (Sandoz), unsymmetrically substituted biphenyls are useful as pharmaceuticals, agricultural chemicals, antioxidants, specialty chemicals, and intermediates therefor; and they can be prepared by a variety of techniques. Unsymmetrically substituted biphenyls include 4-(2,4-dinitrophenyl)phenols.

SUMMARY OF INVENTION

An object of this invention is to provide a novel process for preparing 4-(2,4-dinitrophenyl)phenols.

Another object is to provide such a process wherein the 4-(2,4-dinitrophenyl)phenols are prepared from 1,3-dinitrobenzenes and phenols.

These and other objects are attained by reacting a 1,3-dinitrobenzene having a replaceable hydrogen in the 4-position with a phenol having a replaceable hydrogen in the 4-position in an inert solvent and in the presence of a strong base to form a 4-(2,4-dinitrophenyl)phenol.

DETAILED DESCRIPTION 1,3-Dinitrobenzenes utilizable in the practice of the invention are 1,3-dinitrobenzenes having a replaceable hydrogen in the 4-position, any other free position optionally bearing an inert substituent. A preferred 1,3-dinitrobenzene is 1,3-dinitrobenzene itself.

Phenols that can be used in the invention are phenol itself and other phenols having a replaceable hydrogen in the 4-position. Such phenols, when substituted, have inert substituents, such as alkyl, alkoxy, alkenyl, alkynyl, cycloalkyl, aryl, aralkyl, and alkaryl groups, in one or more of the free positions, generally an alkyl group containing about 1–6 carbons, such as methyl, ethyl, propyl, butyl, t-butyl, pentyl, hexyl, etc. Preferred phenols include phenol and 2,6-dialkylphenols, such as 2,6-di-t-butylphenol, 2,6-diisopropylphenol, 2-t-butyl-6-methylphenol, etc. Although the amount of this ingredient employed is not critical, it has been found that enhanced yields are obtained when the phenol is used in less than a stoichiometric amount.

The solvent used in the reaction of the invention may be any solvent that is inert under the conditions of the reaction, i.e., any solvent that will not prevent the reaction from occurring. Exemplary of the solvents that can be used are inert liquid hydrocarbons, such as benzene, toluene, xylene, hexane, heptane, isooctane, etc.; ethers, such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines, such as pyridine, N-ethylpiperidine, triethylamine, tributylamine, N,N-diphenyl-N-methylamine, N,N-dimethylaniline, etc.; alcohols, such as methanol, ethanol, propanol, etc.; nitriles, such as acetonitrile, etc. However, the preferred solvents are dipolar aprotic solvents, such as dimethylsulfoxide, N,N-dimethylformamide, N,N-dimethylacetamide, dimethylsulfone, tetramethylene, sulfone, N-methylpyrrolidinone, etc. It is not necessary for the solvent to be anhydrous.

Bases useful in the practice of the invention include all bases strong enough to activate the reactants but are generally alkali metal hydrides, hydroxides, or alkoxides, such as sodium or potassium hydride or hydroxide, sodium methoxide, potassium t-butoxide, etc. If desired, the base can be used in conjunction with a phase transfer catalyst, such as a quaternary ammonium salt, a polyethylene glycol, or a suitable crown ether, as in similar processes known in the art. It is preferable to employ at least one molar proportion of base per molar proportion of the 1,3-dinitrobenzene, although lesser amounts are also satisfactory.

The process of the invention is an oxidation-reduction reaction wherein the phenol is coupled to the 4-position of the 1,3-dinitrobenzene. It may be conducted at any suitable temperature, the most appropriate temperature varying with the strength of the base and reactivities of the reactants employed, to prepare the product in a matter of minutes or a few hours. Ambient temperatures are satisfactory when the strongest bases and/or more reactive reactants are used, but higher temperatures, e.g., temperatures up to about 200° C., are more appropriate when somewhat weaker bases and/or less reactive reactants are utilized. If desired, the reaction mixture may contain optional additives, such as potassium permanganate, which increases the yield of product.

The following examples are given to illustrate the invention and are not intended as a limitation thereof.

EXAMPLE I

A mixture of 30 mg (0.75 mmol) of powdered sodium hydroxide, 100 mg (0.59 mmol) of 1,3-dinitrobenzene, 155 mg (0.75 mmol) of 2,6-di-t-butylphenol, and 1.0 mL of dimethylsulfoxide was heated at 80° C. for one hour and poured into 10 mL of 1N HCl, and the resulting aqueous mixture was extracted with three 10 mL portions of diethyl ether. The ether layers were combined, dried over magnesium sulfate, and concentrated. Purification of the residue by preparative thin layer chromatography (PTLC) and crystallization afforded 89 mg (40% yield) of 2,6-di-t-butyl-4-(2',4'-dinitrophenyl)phenol.

EXAMPLE II

Example I was repeated except that the dimethylsulfoxide was replaced with N,N-dimethylformamide. The process afforded 85 mg (39% yield) of crystalline 2,6-di-t-butyl-4-(2',4'-dinitrophenyl)phenol.

EXAMPLE III

Example I was repeated except that the dimethylsulfoxide was replaced with ethanol. The process afforded 25 mg (11% yield) of crystalline 2,6-di-t-butyl-4-(2',4'-dinitrophenyl)phenol.

EXAMPLE IV

Example I was repeated except that the sodium hydroxide was replaced with 84 mg (0.75 mmol) of potassium t-butoxide and the reaction was conducted at ambient temperature. PTLC afforded 114 mg of crude 2,6-di-t-butyl-4-(2',4'-dinitrophenyl)phenol.

EXAMPLE V

Example I was repeated except that the sodium hydroxide was replaced with 30 mg of 60% sodium hydride (0.75 mmol) and the reaction was conducted at ambient temperature. PTLC afforded 58 mg of crude 2,6-di-t-butyl-4-(2',4'-dinitrophenyl)phenol.

EXAMPLE VI

Example I was repeated except that the 2,6-di-t-butylphenol was replaced with 149 mg of 90% 2,6-diisopropylphenol (0.75 mmol) and the reaction was conducted for 20 hours. PTLC afforded 126 mg of crude 2,6-diisopropyl-4-(2',4'-dinitrophenyl)phenol.

EXAMPLE VII

Example I was repeated except that the 2,6-di-t-butylphenol was replaced with 123 mg (0.75 mmol) of 2-t-butyl-6-methylphenol and the reaction was conducted for 2 hours. The process afforded 92 mg (47% yield) of 2-t-butyl-4-(2',4'-dinitrophenyl)-6-methylphenol.

EXAMPLE VIII

Example I was repeated except that the 2,6-di-t-butylphenol was replaced with 71 mg (0.75 mmol) of phenol and the reaction was conducted for 21 hours. The process afforded 25 mg (16% yield) of crystalline 4-(2',4'-dinitrophenyl)phenol.

EXAMPLE IX

Example I was repeated except that the 2,6-di-t-butylphenol was replaced with 128 mg (0.75 mmol) of 2-phenylphenol and the reaction was conducted for 96 hours. PTLC afforded 100 mg of crude 4-(2',4'-dinitrophenyl)-2-phenylphenol.

EXAMPLE X

Example I was repeated except that the 2,6-di-t-butylphenol was replaced with 93 mg (0.75 mmol) of 2-methoxyphenol and the reaction was conducted for 18 hours. The process afforded 30 mg (10% yield) of crystalline 4-(2',4'-dinitrophenyl)-2-methoxyphenol.

EXAMPLE XI

Example I was repeated except that 118 mg (0.75 mmol) of ground potassium permanganate were included in the reaction mixture and the reaction was conducted for two hours. The process afforded 150 mg (68% yield) of crystalline 2,6-di-t-butyl-4-(2',4'-dinitrophenyl)phenol.

EXAMPLE XII

Example I was repeated except that 122 mg (0.73 mmol) of 1,3-dinitrobenzene and 100 mg (0.48 mmol) of 2,6-di-t-butylphenol were used, and the reaction was conducted for two hours. The process afforded 110 mg (61% yield) of crystalline 2,6-di-t-butyl-4-(2',4'-dinitrophenyl)phenol.

It is obvious that many variations can be made in products and processes set forth above without departing from spirit and scope of this invention.

I claim:

1. A process which comprises reacting (a) a 1,3-dinitrobenzene having a replaceable hydrogen in the 4-position with (b) a phenol having a replaceable hydrogen in the 4-position and selected from the group consisting of phenol and substituted phenols bearing at least one inert ring substituent selected from alkyl, alkoxy, alkenyl, alkynyl, cycloalkyl, aryl, aralkyl, and alkaryl groups in an inert solvent and in the presence of an alkali metal hydride, hydroxide, or alkoxide to form a 4-(2,4-dinitrophenyl)phenol.

2. The process of claim 1 wherein the 1,3-dinitrobenzene is 1,3-dinitrobenzene.

3. The process of claim 1 wherein the phenol is phenol.

4. The process of claim 1 wherein the phenol is a substituted phenol bearing at least one inert substituent on the ring.

5. The process of claim 4 wherein the substituted phenol is a 2,6-dialkylphenol.

6. The process of claim 1 wherein the alkali metal compound is an alkali metal hydroxide.

7. The process of claim 6 wherein the alkali metal hydroxide is sodium hydroxide.

8. The process of claim 1 wherein the inert solvent is a dipolar aprotic solvent.

9. The process of claim 8 wherein the dipolar aprotic solvent is dimethylsulfoxide.

* * * * *